US006713444B1

(12) United States Patent
Garcia et al.

(10) Patent No.: US 6,713,444 B1
(45) Date of Patent: *Mar. 30, 2004

(54) BUFORIN I AS A SPECIFIC INHIBITOR AND THERAPEUTIC AGENT FOR BOTULINUM TOXIN B AND TETANUS NEUROTOXINS

(75) Inventors: Gregory E. Garcia, Germantown, MD (US); Richard K. Gordon, Potomac, MD (US); Debbie R. Moorad, Rockville, MD (US); Bhupendra P. Doctor, Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/570,023

(22) Filed: May 12, 2000

Related U.S. Application Data
(60) Provisional application No. 60/134,216, filed on May 14, 1999.

(51) Int. Cl.[7] .......................... A61K 38/00; C07K 14/00
(52) U.S. Cl. ............................ 514/2; 514/13; 514/21; 530/324; 530/326; 530/333; 530/344; 424/239.1; 424/9.1; 435/252.7
(58) Field of Search .................... 514/12, 13, 21; 530/324, 326, 333, 344; 424/239.1, 9.1; 435/252.7

(56) References Cited

U.S. PATENT DOCUMENTS 5,936,063 A * 8/1999 Kim et al. ................. 530/324
6,573,244 B1 * 6/2003 Gordon et al. ............... 514/15

OTHER PUBLICATIONS

Park et al., A novel antimicrobial peptide form bufo bufo gargarizans. Biochem. Biophys. Res. Commun. 218, 408–413 (1996).*
Garcia et al., Botulinum B toxin activity is inhibited by Buforin I. FASEB Journal vol. 12, No. 8, pp A1472. (Apr. 1998).*

* cited by examiner

Primary Examiner—Christopher S. F. Low
Assistant Examiner—Chih-Min Kam
(74) Attorney, Agent, or Firm—Elizabeth Arwine

(57) ABSTRACT

The compounds of the invention are generally described by the formula:

$$X_1X_2B_3X_4B_5X^*_6X_7X_8$$
$$B_9X_{10}B_{11}X_{12}B_{13}X_{14}$$
$$B_{15}X_{16}B_{17}X^*_{18}X^*_{19}B_{20}$$
$$X_{21}X_{22}X_{23}Q_{24}F_{25}Z^*_{26}X_{27}$$
$$X_{28}B_{29}X_{30}B_{31}B_{32}X_{33}X_{34}$$
$$B_{35}B_{36}X_{37}Z_{38}Z_{39}$$

(1)

and the salts, esters, amides, and acyl forms thereof. Up to 15 amino acids may be truncated from the N-terminus and up to 6 amino acids may be truncated from the C-terminus. Each position represented by a letter indicates a single amino acid residue wherein B is a basic or polar/large amino acid or a modified form thereof; X is a small or hydrophobic amino acid or a modified form thereof; X* is a small or polar/large amino acid or a modified form thereof; Z is a polar/large or hydrophobic amino acid or a modified form thereof; Z* is Proline or a polar/large or hydrophobic amino acid or a modified form thereof. These compounds may be used to inhibit the protease activity of Botulinum B and tetanus toxins.

12 Claims, 8 Drawing Sheets

B-I
A G R G K Q G G K V R A K A K T R S S R A G L Q F P V G R V H R L L R K G N Y
B-I R11L
A G R G K Q G G K V L A K A K T R S S R A G L Q F P V G R V H R L L R K G N Y
B-I R11L, K15L, S19L
A G R G K Q G G K V L A K A L T R L S R A G L Q F P V G R V H R L L R K G N Y
FIG. 6A
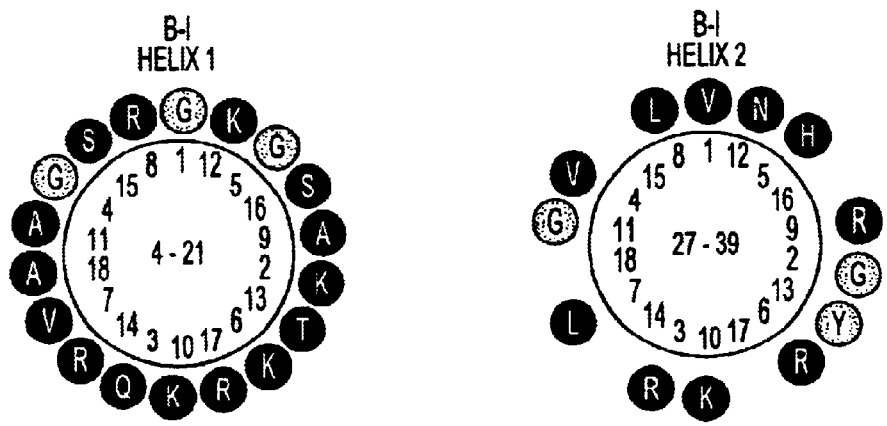
FIG. 6B
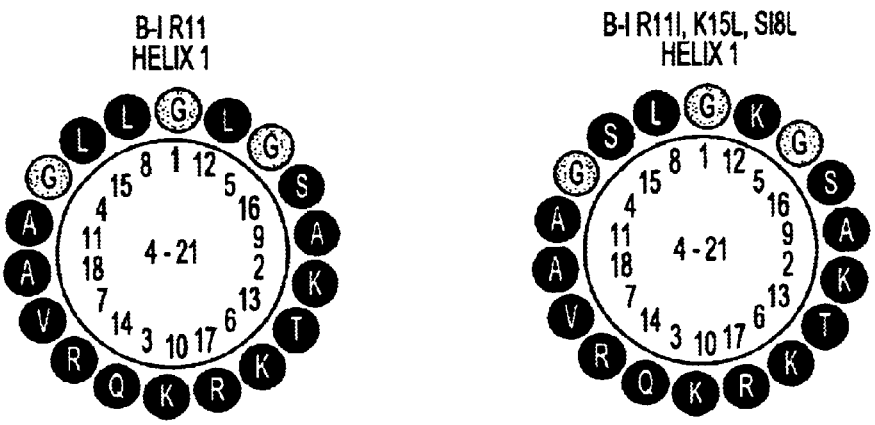
FIG. 6C

FIG. 7

BUFORIN I AS A SPECIFIC INHIBITOR AND THERAPEUTIC AGENT FOR BOTULINUM TOXIN B AND TETANUS NEUROTOXINS

CROSS REFERENCE TO RELATED APPLICATIONS

This application is based on provisional application No. 60/134,216 filed May 14, 1999.

ACKNOWLEDGMENT OF GOVERNMENT INTEREST

This invention was made by employees of the United States Army. The government has rights in the invention

TECHNICAL FIELD

The invention relates to a class of peptide and peptide-like compounds, "Bufornins" which inhibit the enzymatic activity of Botulinum toxin B and Tetanus neurotoxins.

BACKGROUND OF THE INVENTION

The Botulinum toxins (Bttxs) are among the most potent toxins to animals, e. g. the $LD_{50}$ in mice is about 1 ng/kg. Bttxs comprise a family of seven distinct serotypes (A–G). Bttxs are composed of two subunits comprising a 100 kdal nerve-cell target heavy chain and a 50 kdal endoproteolytically active light chain. These toxins are Zn-metalloproteases and contain a Zn-protein binding motif HEXXH.

However, Zn-metalloprotease inhibitors, such as angiotensin converting enzyme inhibitors, captopril and phosphoramidon, are not effective inhibitors of Bttxs. Although Zn-chelators inhibit Bttx protease activity in vitro, they merely delay the protease activity in vivo and in tissue preparations comprising intact nerve and muscles cells and/or tissues. Furthermore, some Zn-chelators are toxic at concentrations necessary to delay the Bttx protease activity. Although dithiocarbamates inhibit other Zn-containing proteins such as SOD, they are ineffective against the Bttx serotype B (BttxB). Clearly, inhibitors of the various Bttx serotypes, such as BttxB, are needed.

BttxB specifically cleaves synaptobrevin (VAMP2) between glutamine 76 and phenylalanine 77 (QF bond or cleavage site). There is an obligatory requirement for a relatively long substrate for the in vivo target VAMP2 as shown by efforts to produce a minimum length substrate. It has been shown that 30 amino acids of VAMP2 are required and 40 amino acids of VAMP2 are required for optimum cleavage. See Shone, C. C. et al. (1993) Eur. J. Biochem 217:965–971. V2, a peptide derived from VAMP2, is a sequence of 10 amino acids located 4 residues upstream from the cleavage site, and was found to inhibit Bttx activity. See Pellizzari R. et at. (1996) J. Biol. Chem. 271:20353–20358. In VAMP2, a mutation of the C-terminal amino acids had little effect; whereas a helix disrupting substitution of Pro for Ala inhibited BttxB activity by 28%. Further, replacement of several negatively charged amino acids led to almost complete inacivity. See Whitcome, M, et al. (1996) FEBS Let. 386:133–136).

Computer-aided secondary structure analysis of VAMP2 predicted two stretches of α-helical structure flanking the cleavage site QF. See Witcome, M. R. et al. (1996) FEBS Let. 386: 133–136. Computer-aided tertiary structure analysis indicates that the two helices could self associate to form a supersecondary structure of a helix bundle with the helices separated by a reverse turn. See Lebeda F. J., et al. (1996) Med. Defense Biosci. Rev. 204.

The above results indicate that more than just the QF bond is required to be recognized by the toxin for substrate cleavage.

Recently, a new class of compounds have been discovered, which have a characteristic conformation and the QF bond, that inhibit the Bttx protease activity. These compounds and their uses are disclosed herein below.

SUMMARY OF THE INVENTION

The invention is directed to a class of peptides and peptide-like compounds, Buforinins, which have an internal QF bond and the ability to inhibit BttxB protease activities. As the tetanus toxin cleavage site is the same as BttxB, Buforinins may also competitively inhibit tetanus protease activity.

Thus, in one aspect, the invention is directed to compounds of the formula:

$$X_1X_2B_3X_4B_5X^*_6X_7X_8$$

$$B_9X_{10}B_{11}X_{12}B_{13}X_{14}$$

$$B_{15}X_{16}B_{17}X^*_{18}X^*_{19}B_{20}X_{21}$$

$$X_{22}X_{23}Q_{24}F_{25}Z^*_{26}X_{27}$$

$$X_{28}B_{29}X_{30}B_{31}B_{32}X_{33}X_{34}$$

$$B_{35}B_{36}X_{37}Z_{38}Z_{39} \qquad (1)$$

and the salts, esters, amides, and acyl forms thereof. Up to 15 amino acids may be truncated from the N-terminus and up to 6 amino acids may be truncated from the C-terminus. Each position represented by a letter indicates a single amino acid residue wherein B is a basic or polar/large amino acid or a modified form thereof; X is a small or hydrophobic amino acid or a modified form thereof; X* is a small or polar/large amino acid or a modified form thereof; Z is a polar/large or hydrophobic amino acid or a modified form thereof; Z* is Proline or a polar/large or hydrophobic ammo acid or a modified form thereof. As described below, one or more of the peptide linkages between the amino acid residues may be replaced by a peptide linkage mimic.

In other a the invention is directed to recombinant materials useful for the production of those peptides of the invention that contain gene-encoded amino acids, as well as plants or animals modified to contain expression systems for the production of these peptides. The invention also includes methods to prepare and manipulate these recombinant materials.

In addition, the invention is directed to pharmaceutical compositions containing the compounds of the invention as active ingredients and to compositions which contain expression systems for the production of the peptides. The invention is also directed to methods to prepare the invention compounds synthetically, to antibodies specific for these compounds, and to the use of the compounds as preservatives, therapeutics, and prophylactics.

The invention is also directed to the use of the compounds of the invention in assays for detection of BttxB and Tttx by the use of selective inhibition and for determining inhibitors and substrates for a given toxin.

The present invention relates to materials, compositions, kits and methods for inhibiting the enzymatic activity of Botulinum toxin B and Tetanus neurotoxins.

The invention further relates to materials, compositions, kits and methods for preventing or treating toxic poisoning such as Botulinum toxin B and tetanus poisoning. The kits can an provide single or multiple dosage and can include other conventional ancillary materials such as instructions, solutions and compositions needed for operation. The compositions and solutions may be placed in containers, lest tubes, etc. Containers could be similar to those employed in insect/snake bite kits that includes an injector which provides the Buforinin, and TCEP in separate chambers. If chaotropes are present, they are separately included in one or more containers.

A kit for determining whether a sample contains a Buforinin, the amount of said Buforinin or the type of said Buforinin may include antibodies immunospecific for Buforinins.

A kit for determining whether a sample contains a Botulinum toxin or the type of the Botulinum toxin may include antibodies immunospecific for at least one Buforinin having an interaction with a Botulinum toxin. Likewise, a kit for determining whether a sample contains a Tetanus toxin would include antibodies immunospecific for at least one Buforinin having an interaction with a Tetanus toxin.

Another embodiment includes Buforin I along with one or more known peptide inhibitors associated with the decontamination of Botulinum B and/or Tetanus toxins. Additionally, the kits may also include a stable peptide mixture or powder which includes Buforinin for sprinkling over food or wounds for detoxification.

DESCRIPTION OF THE DRAWINGS

This invention is further understood by reference to the drawings wherein:

FIG. 1 shows that Substance P is not a substrate of BttxB.

FIG. 2 shows that Buforinins are not substrates of BttxB.

In FIG. 6, Helix 1 and 2 are the helices predicted for sequence upstream and downsteam of the QF site respectively (see Table 2). Mutants were selected to increase the amphipathicity of the helix indicated. B-I Helix 2 is shown as the companion to which Helix 1 is predicted to associate. A Amino acid sequences. B. Helical wheel projections of Buforin-I. Helix-1 is the predicted upstream helix of the QF site and Helix-2 is the downstream helix. The helix amino acids are indicated in the wheel center. C. Helical wheel projections of mutant Buforinins. The amino acid order is indicated by the concentric numbering. For A, B, and C the color code is as follows: dark gray: hydrophobic; light gray: hydrophilic; stippled gray: other; with the amino acids indicated within the circles. FIG. 6A is a comparison of the amino acid sequences of Buforin I, and mutant B-I R11L and mutant B-I R11L, K15L, S18L. FIG. 6B shows helical wheel projections for Buforin I of Helix I and Helix 2. FIG. 6C shows helical wheel projections for Helix 1 of mutants B-I R11L and B-I R11L, K15L, S18L.

FIG. 7 shows inhibition of Botulinum toxin B endoprotease activity with peptide OSP (Sequence:

ThrArgSerArgAlaLysGlyLeuGln-
PheProGlyLeuLeuValHisArgLysGlyAsnTyr (SEQ ID NO: 7)).

Figure 8:
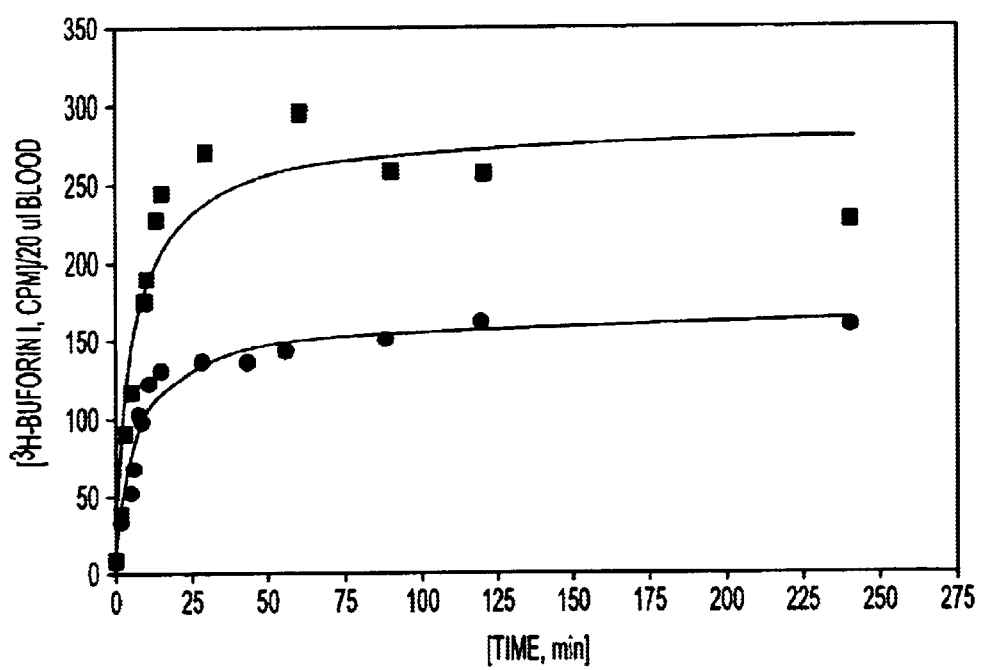

FIG. 8 shows the rapid uptake of Buforin I in to blood over time.

DETAILED DESCRIPTION OF THE INVENTION

Figure 1:
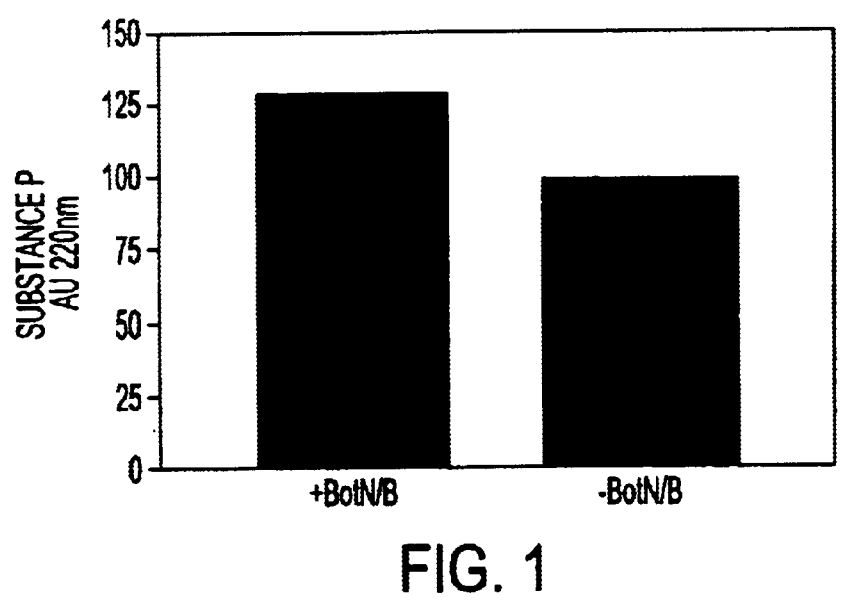

In our search for BttxB inhibitors, peptides that contain the QF cleavage site but are not identical in primary sequence to VAMP2 surrounding the QF site were investied Substance P, an 11 amino acid peptide containing the QF bond, is not a substrate of BttxB. See Example 1 and 2; and FIG. 1. This result supports the preferred helix-turn-helix and/or long substrate hypothesis.

Figure 2:
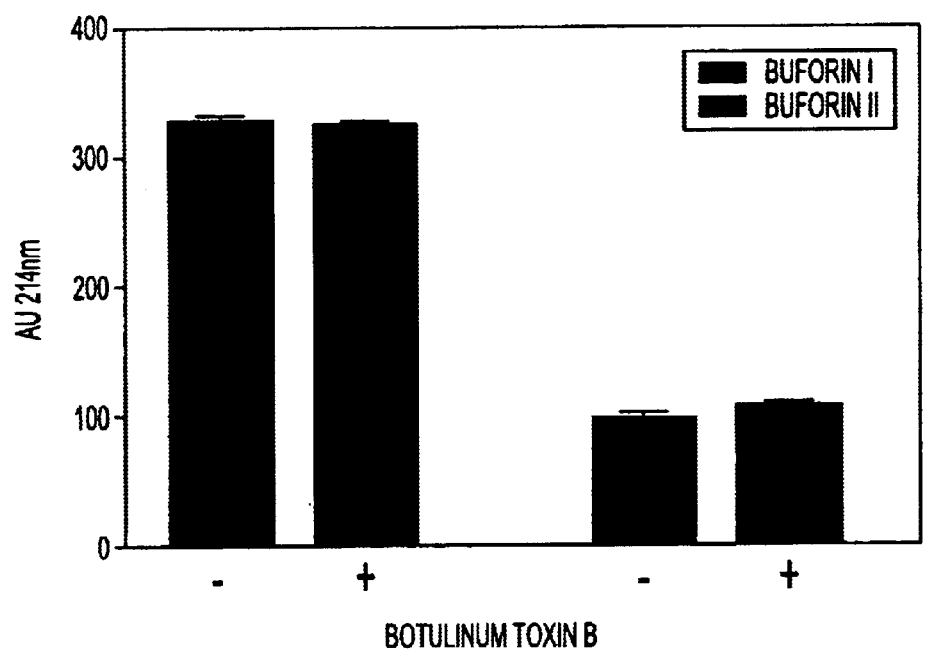
Figure 3:
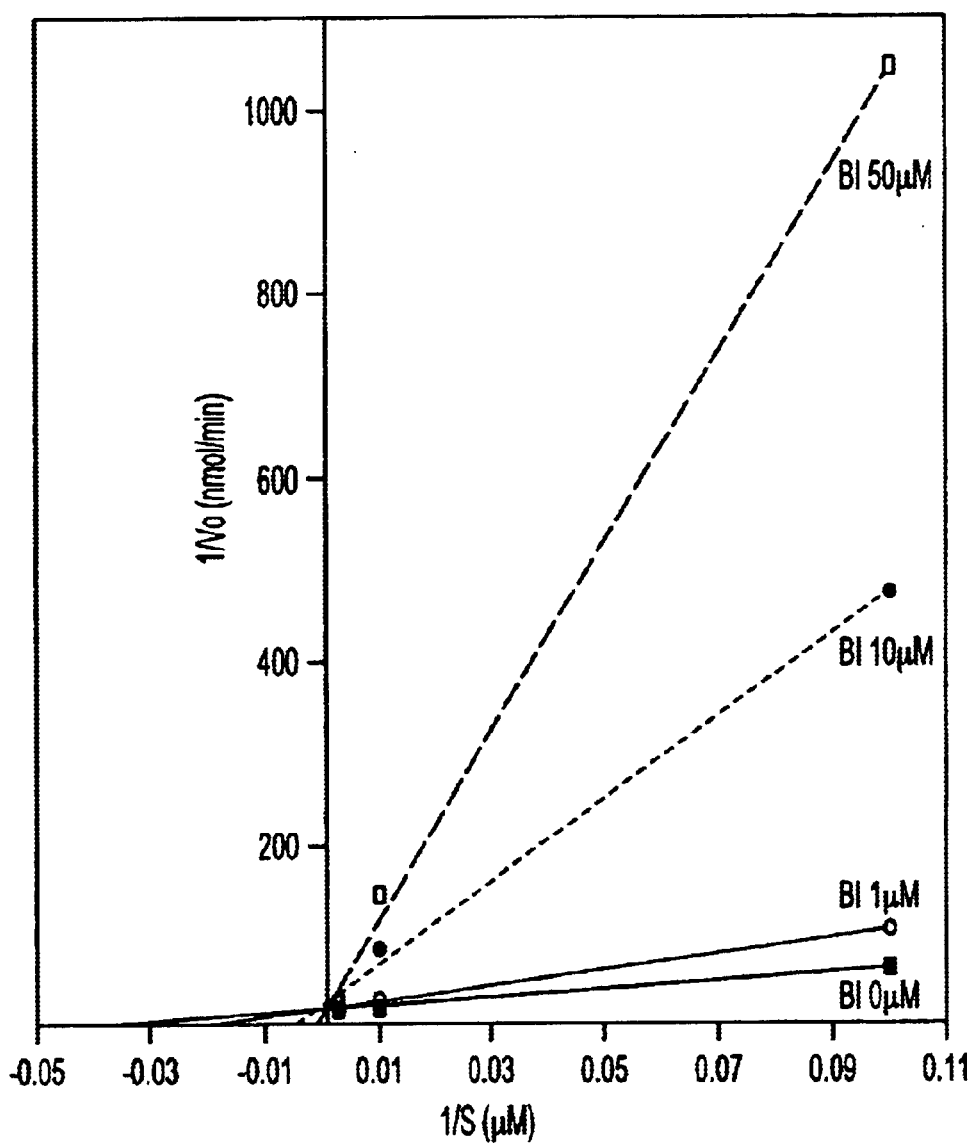
FIG. 3 shows a double reciprocal plot of inhibition of BttxB endoprotease activity by Buforin I.
Figure 4:
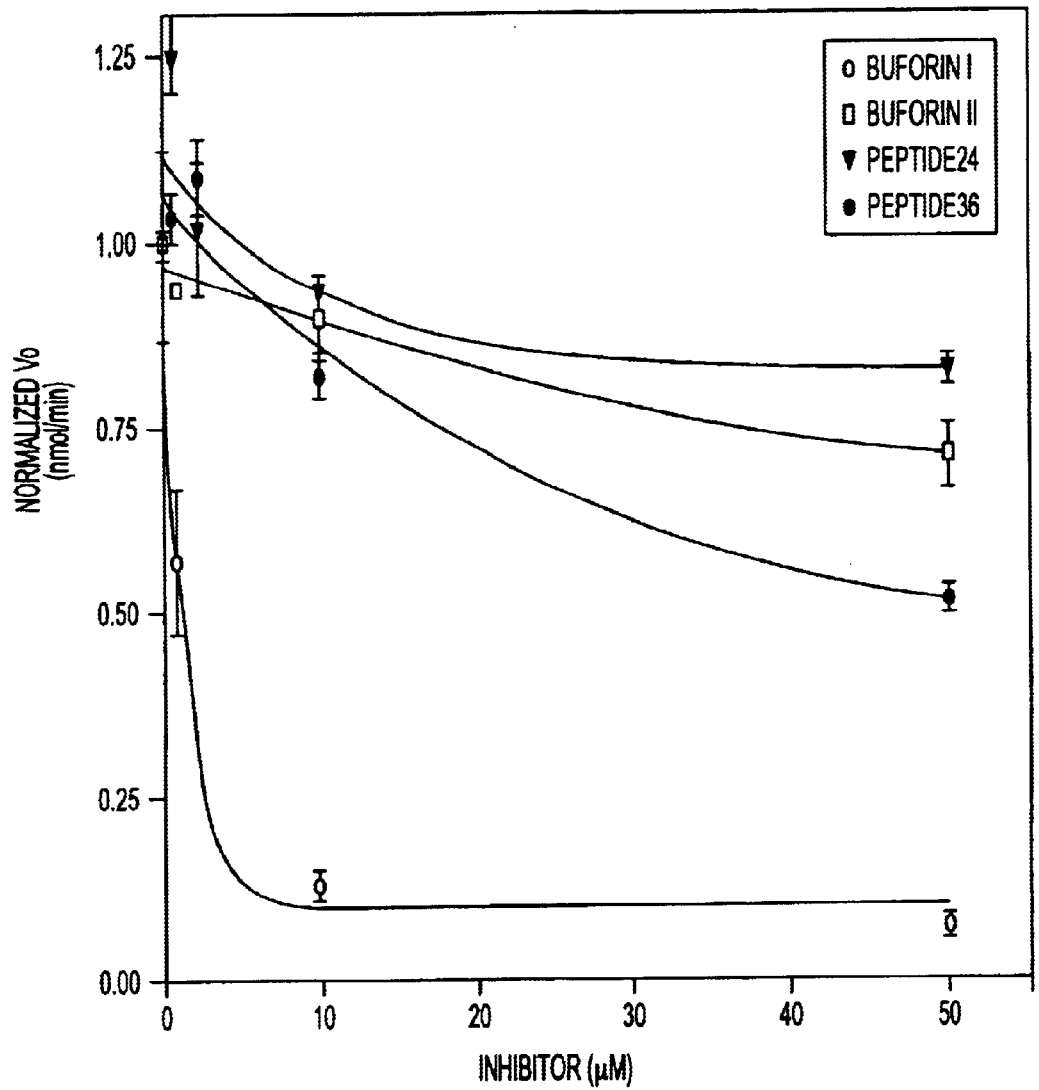
FIG. 4 illustrates the inhibition of BttxB endoprotease activity by various Buforinins.

Buforin I (B-I) is a peptide isolated from the stomach of the Asian toad *Bufo bufo gargarizans* which has a QF bond. Therefore, the endopeptidase assay, below, was used to determine if B-I is a substrate or an inhibitor of BttxB protease activity. B-I was found not to be a substrate for BttxB and that B-I dose-dependency and competitively inhibits BttxB activity. See FIGS. 2 and 3. The extent of inhibition gave an $IC_{50}=1\times10^{-6}$ M. See FIG. 4. This was a surprising result as B-I is only 18% homologous for conserved amino acids with VAMP2 55–94. See Table I.

TABLE I

Sequence alignment of VAMP2, Buforin I and Buforin I derivative peptides

| Peptide | Sequence |
|---|---|
| VAMP2$_{55-94}$ | GluArgAspGlnLysLeuSerGluLeuAspAspArgAlaLeuGlnAlaGlyAlaSerGlnPhe GluThrSerAlaAlaLysLeuLysArgLysTyrTrpTrpLysAsnLeuLys (SEQ ID NO:8) |
| Buforin I[a] | AlaGlyRArgGlyLysGlnGlyGlyLysValArgAlaLysAlaLysThrArgSerSerArgAla GlyLeuGlnPheProValGlyArgValHisArgLeuLeuArgLysGlyAsnTyr (SEQ ID NO:1) |

TABLE I-continued

Sequence alignment of VAMP2, Buforin I and Buforin I derivative peptides

| Peptide | Sequence |
|---|---|
| Burorin II[b] | ThrArgSerSerArgAlaGlyLeuGlnPheProValGlyArgValHisArgLeuLeuArgLys (SEQ ID NO:2) |
| Peptide24[c] | ThrArgSerSerArgAlaGlyLeuGlnPheProValGlyArgValHisArgLerLeuArgLys GlyAsnTyr (SEQ ID NO:3) |
| Peptide36[c] | AlaGlyArgGlyLysGlnGlyGlyLysValArgAlaLysAlaLysThrArgSerSerArgAlaGly LeuGlnPheProValGlyArgValHisArgLeuLeuArglys (SEQ ID NO:4) |

[a]Archer, B. T. III., et al. (1990) J. Biol. Chem. 265 (28), 17267–17273.
[b]Park C. B., et al. (1996)
[c]Garcia, G. E., et al. (1998)

Truncated B-I peptides were evaluated with our endopeptidase activity assay. The truncated peptides evaluated were Peptide 36 which contains amino acids 1–36 of B-I and Peptide 24 which contains amino acids 16–39 of B-I. Like B-I, these truncated peptides were not substrates of BttxB; however, the truncated peptides are less effective inhibitors of BttxB activity as B-I. See FIG. 2. Peptide 36 was about 50% as effective as B-I. Peptide 24 was about 25% as effective as B-I. Buforin II (B-II), which contains amino acids 16–36 of B-I, was also evaluated and found to be 25% as effective as B-I.

Figure 5:
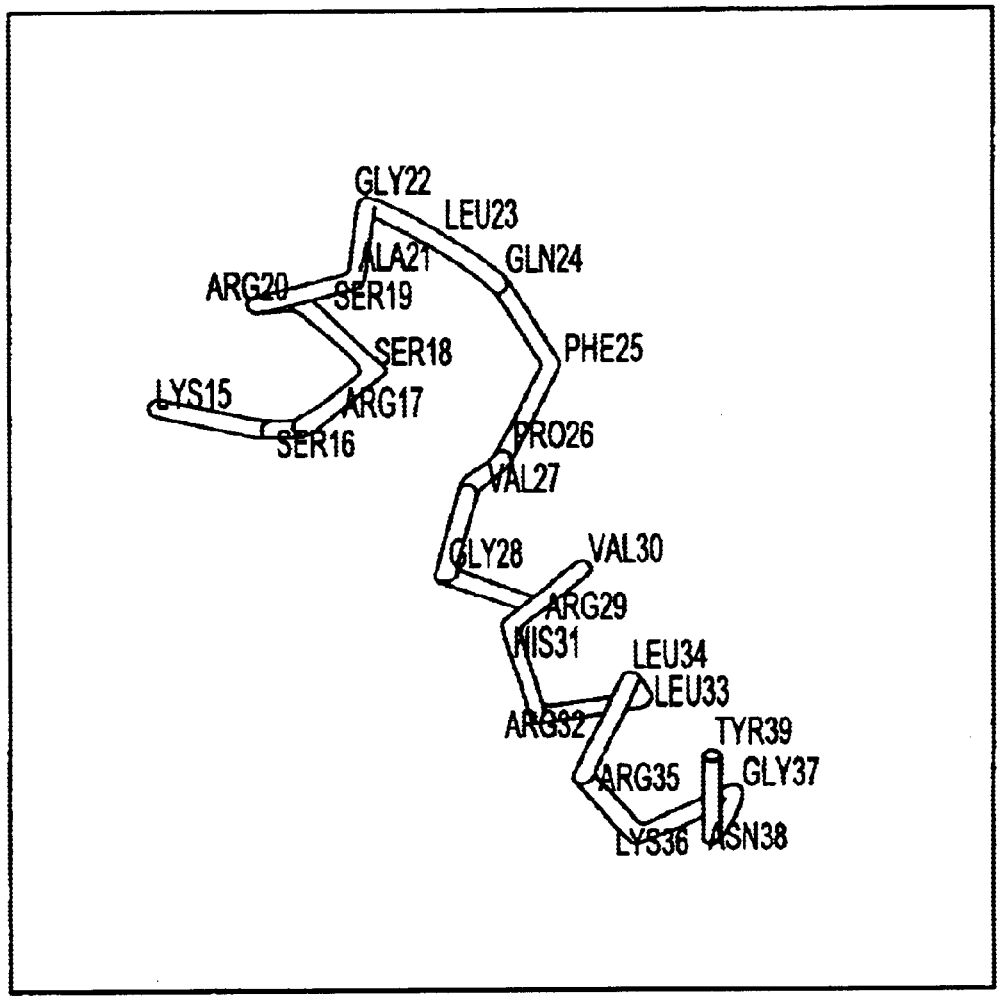
FIG. 5 illustrates the X-ray crystallographic structure of avian chromosomal protein histone octamer H2A residues Lys15-Try39 produced by Brookhaven Protein Database #1HIO.

B-I is derived from histone protein 2A (H2A) of the toad which is nearly identical to the sequence of avian H2A. See Table 2 and see Park, C. B., et al. (1996) Biochem. Biophys. Res. Com 218:408–413. X-ray crystallographic analysis of the chicken histone protein particle shows that, for the region K15 to Y39, there are helices upstream and downstream of the QF site. See FIG. 5 and see Arents, G., et al. (1991) PNAS 88:10148–52 and Wang, S. W., et al. (1985) Nucleic Acids Res. 13:1369–138. Also, NMR analysis of B-II shows that the region upstream from the QF site could form α-helix. See Yi, et al. (1996) FEBS Lett. 398:87–90.

TABLE II

H2A comparison of chicken to toad for relevant amino acid sequences

| Source | Database[GB] Accession no. | | % Homology[a] |
|---|---|---|---|
| Bulb bufo gagarizans | BBU70133 | GlyArgGlyLysGlnGlyGlyLysValArgAlaLysThr ArgSerSerArgAlaGlyLeuGlnPheProValGlyArg ValHisArgLeuLeuArgLysGlyAsnTyr (SEQ ID NO:9) | |
| Gallus gallus | X02218 | GlyArgGlyLysGlnGlyGlyLysAlaArgAlaLysAla LysSerArgSerSerArgAlaGlyLeuGlnPheProVal GlyArgValHisArgLeuLeuArgLysGlyAsnTyr (SEQ ID NO:10) | 100 |

The suffix [GB] signifies accession numbers in the GenBank database.
[a]Homology to toad sequence. Similarity; basic: Arg, Lys; acidic: Asp, Glu; polar: Asn, Gln; hydrophobic: Ala, Ile, Leu, Met, Val; aromatic: Phe, Tyr, Trp; size: Ala, Ser, Thr.
[1] Kim, H. S., Park, C. B., Kim, M. S., Kim, S. C. (96) Biochem. Biophys. Res. Comm. 229:381–387.
[2] Wang, S. W., Robins, A. J., d = Andrea, R. Wells. J. R. (85) Nucleic Acids Res. 13:1369–1387.

These results indicate that there is potential for long Buforinins to form a similar supersecondary structure of a reverse turn with helix bundling. See Table 3. Therefore, a new class of peptides, "Buforinins" which includes Buforin I (39 amino acids), Buforin II (21 amino acids), Peptide 36 and Peptide 24, and other analogous peptides having a QF bond, that competitively inhibit BttxB protease activity was defined.

TABLE III

Computer-Aided Secondary Structure Predictions

| | |
|---|---|
| VAMP2$_{55-94}$ | GluArgAspGlnLysLeuSerGluLeuAspAspArgAlaLeuGln AlaGlyAlaSerGlnPheGluThrSerAlaAlaLysLeuLysArgLys TyrTrpTrpLysAsnLeuLys (SEQ ID NO:8) |
| Gibrat$^b$ | HHHHHHHHHHHHHHHHHCCHHHHHHHHHHHHHH TTHHTCT |
| Nnpredict$^c$ | --------HH-HHHHHHH---HHHHHHHHHHHHHHHH---- |
| B-I | AlaGlyArgGlyLysGlnGlyGlyLysValArgAlaLysAlaLys ThrArgSerSerArgAlaGlyLeuGlnPheProValGlyArgValHis ArgLeuLeuArgLysGlyAsnTyr (SEQ ID NO:12) |
| Gibrat | HTTTTTCCEEEEHHHHHHHHHCTEEEEHHHHEEEET TTC |
| Nnpredict B-I | ---------EHE-----------E----HHHHHHHH---- |
| Truncated 5 amino acids on both ends | GlnGlyGlyLyValArgAlaLysAlaLysThrArgSerSerArg AlaGlyLeuGlnPheProValGlyArgValHisArgLeuLeu (SEQ ID NO:11) |
| Gibrat | HCCHHEEHHHHHHHHHCCEEEECHEHEEE |
| Nnpredict | --------E----HHHHHH |

$^a$H, helix; E, sheet; C, coil; T, turn; -, no prediction. QF cleavage site is indicated in bold.
$^b$Garnier J. et al. (1987) J. Mol. Biol. 120:97–120.
$^c$McCleland, D. G., Rumelhart D. E. In Explorations in Parallel Distributed Processing.
3: 318–362.
1988. MIT Press, Cambridge MA; Kneller D. G., et al. (1990) J. Mol. Biol. 214:171–182.

These Bufornins are generally described by the formula:

$X_1X_2B_3X_4B_5X^*_6X_7X_8B_9$ $X_{10}B_{11}X_{12}B_{13}X_{14}B_{15}X_{16}$ $B_{17}X^*_{18}X^*_{19}B_{20}X_{21}X_{22}X_{23}$ $Q_{24}F_{25}Z^*_{26}X_{27}X_{28}B_{29}X_{30}$ $B_{31}B_{32}X_{33}X_{34}B_{35}B_{36}X_{37}$ $Z_{38}Z_{39}$ (1)

and the salts, esters, amides, and acyl forms thereof. Up to 15 amino acids may be truncated from the N-terminus and up to 6 amino acids may be truncated from the C-terminus. Each position represented by a letter indicates a single amino acid residue wherein B is a basic or polar/large amino acid or a modified form thereof; X is a small or hydrophobic amino acid or a modified form thereof; X is a small or polar/large amino acid or a modified for thereof; Z is a polar/large or hydrophobic amino acid or a modified form thereof; Z* is Proline or a polar/large or hydrophobic amino acid or a modified form thereof. As described below, one or more of the peptide linkages between the amino acid residues may be replaced by a peptide linkage mimic.

The invention compound include those represented by formula (1) as well as analogous peptides. "Analogous" forms are peptides which retain the ability to form the supersecondary structure, alpha-helical-turn-alpha-helical configuration and inhibit BttxB protease activity in reaction with the toxin (since it apparently has no secondary structure in aqueous solution). "Analogous" forms also include peptides having amino acid sequences which mimic the conformational structure of either B-I or B-II and interact with BttxB to inhibit its protease activity. "Analogous" forms also include peptides which are isolatable from the amphibian stomach and inhibit BttxB protease activity.

The amino terminus of the peptide may be in the free amino form or may be acylated by a group of the formula RCO-, wherein R represents a hydrocarbyl group of 1–6C.

The hydrocarbyl group is saturated or unsated and is typically, for example, methyl, ethyl, i-propyl, t-butyl, n-pentyl, cyclohexyl, cyclohexene-2-yl, hexene-3-yl, hexyne4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

The peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The amino acids in the peptides of the invention may be those encoded by the gene or analogs thereof, and may also be the D-isomers thereof. A preferred embodiment is a compound of the formula (1) where the compound is resistant to protease activity by having at least some of its residues in the D-configuration, yet retains the ability to inhibit BttxB protease activity.

The amino acid notations used herein are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |

-continued

| Amino Acid | One-Letter Symbol | Three-Letter Symbol |
| --- | --- | --- |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The compounds of the invention are peptides or peptide-like compounds which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a or lesser extent. To fit the definition of "charged," a significant percentage (at least approximately 25%) of the individual molecules are charged at the relevant pH. The degree of attraction or repulsion red for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

| | |
| --- | --- |
| Acidic | Aspartic acid and Glutamic acid |
| Basic | Noncyclic: Arginine, Lysine |
| | Cyclic: Histidine |
| Small | Glycine, Serine, Alanine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, i.e. helix structure disruptions. Therefore, proline may only be allowed in position 26 where it would help to disrupt the helix structures found on both sides of the QF cleavage site and force the helix-turn-helix structure.

Cysteine residues are also not included in these classifications since their capacity to form disulfide bonds to provide secondary structure may override the general polarity/nonpolarity of the residue. However, if a cysteine, which is, technically speaking, a small amino acid, is modified so as to prevent its participation in secondary structure, those locations indicated "S" in the compound of formula (1) may be inhabited by such modified cysteine residues.

There are no cysteine or methionine in any of the sequences (VAMP2 substrate, B-I, B-II, Peptide 24, Peptide 36). The side chain of cysteine is somewhat hydrophobic, but it is highly reactive. The sulfur moiety has the potential to react with the sulfur in other cysteine to from a cystine or disulfide bond. If a single cysteine is introduced then dimerization may occur between two buforoxins. If more than one cysteine is introduced then polymerization could occur. Clearly, the substitution of cysteine near the cleavage site with resultant dimerization or polymerization could interfere with the helix-turn-helix structure thought to be necessary for inhibition and produce steric interference for the interaction of the target protein and buforinin. Another problem associated with cysteine and methionine residues is the potential for oxidation to cysteic acid or methionine sulfoxide or methionine sulfone respectively. These conversions would significantly alter the peptide properties since a hydrophobic weakly polar or ionizable form would be converted to an acidic or strongly polarized form. However, it may be advantageous to incorporate cysteine on either end of a Buforinin for use as a reactive site to label a Buforinin with fluorescent markers where the aforementioned problems may be minimized.

The "modified" amino acids that may be included in the Buforinins are gene coded amino acids which have been processed after translation of the gene, e.g., by the addition of methyl groups or derivatization through covalent linkage to other substituents or oxidation or reduction or other covalent modification. The classification into which the resulting modified amino acid fills will be determined by the characteristics of the modified form. For example, if lysine were modified by acylating the ϵ-amino group, the modified form would not be classed as basic but as polar/large amino acid.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalnine (2-Nal); 1,2,3,4-tetrahydroisoquinoline-3 carboxylic acid (Tic); β-2-thienylalanine (Thi); methionine sulfoxide (MSO); and homoarginine (Har). These also fall conveniently into particular categories.

Based on the above definitions,

Sar, beta-Ala and Aib are small;

t-BuA, t-BuG, N-MeIle, Nle, Mvl, Cha, Phg, Nal, Thi and Tic are hydrophobic;

2,3-diaP, Orn and Har are basic;

Cit, Acetyl Lys and MSO are neutral/polar/large.

The various omega-amino acids are classified according to size as small (beta-Ala and 3-aminopropionic) or as large and hydrophobic (all others).

Other amino acid substitutions, which are not gene encoded, are included in peptide compounds within the scope of the invention and can be classified within this general scheme according to their structure. For example, D-amino acid substitutions would be desirable to circumvent potential stability problems due to endogenous protease activity; especially important for an oral dosage route.

In all of the Buforinins of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH=CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al, *Tetrahedron Lett* (1983) 24:4401–4404 (—C(OH) CH$_2$—); and Hruby, V. J., *Life Sci* (1982) 31:189–199 (—CH$_2$—S—).

In preferred embodiments of the compounds of the formula (1):

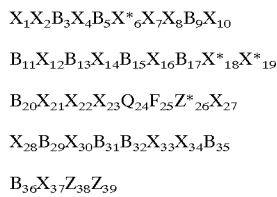

$X_1$ is Glycine, Serine, Threonine, Isoleucine, Leucine, Valine, or preferably Alanine;

$X_2$ is Alanine, Serine, Threonine, Isoleucine, Leucine, Vie, or preferably Glycine;

$B_3$ is Histidine, Lysine, Asparagine, Glutamine, or preferably Arginine;

$X_4$ is Alanine, Serine, Threonine, Isoleucine, Leucine, Valine, or preferably Glycine;

$B_5$ is Arginine, Histidine, Asparagine, Glutamine, or preferably Lysine;

$X^*_6$ is Alanine, Glycine, Serine, Threonine, Asparagine, or preferably Glutamine;

$X_7$ is Alanine, Serine, Threonine, Isoleucine, Leucine, Valine, or preferably Glycine;

$X_8$ Alanine, Serine, Threonine, Isoleucine, Leucine, Valine, or preferably Glycine;

$B_9$ is Arginine, Histidine, Asparagine, Glutamine, or preferably Lysine;

$X_{10}$ is Alanine, Glycine, Serine, Threonine, Isoleucine, Leucine, or preferably Valine;

$B_{11}$ is Histidine, Lysine, Asparagine, Glutamine, or preferably Arginine;

$X_{12}$ is Glycine, Serine, Threonine, Isoleucine, Leucine, Valine, or preferably Alanine;

$B_{13}$ is Arginine, Histidine, A Glutamine, or preferably Lysine;

$X_{14}$ is Glycine, Serine, Threonine, Isoleucine, Leucine, Valine, or preferably Alanine;

$B_{15}$ is Arginine, Histidine, Asparagine, Glutamine, or preferably Lysine;

$X_{16}$ is Alanine, Glycine, Serine, Isoleucine, Leucine, Valine, or preferably Threonine;

$B_{17}$ is Histidine, Lysine, Asparagine, Glutamine, or preferably Arginine;

$X^*_{18}$ is Alanine, Asparagine, Glutamine, Glycine, Threonine, or preferable Serine;

$X^*_{19}$ is Alanine, Asparagine, Glutamine, Glycine, Threonine, or preferable Serine;

$B_{20}$ is Histidine, Lysine, Asparagine, Glutamine, or preferably Arginine;

$X_{21}$ is Glycine, Serine, Threonine, Isoleucine, Leucine, Valine, or preferably Alanine;

$X_{22}$ is Alanine, Serine, Threonine, Isoleucine, Leucine, Valine, or preferably Glycine;

$X_{23}$ is Asparagine, Glutamine, Alanine, Serine, Threonine, Isoleucine, Glycine, Valine, or preferably Leucine;

$Z^*26$ is Asparagine, Glutamine, Phenylalanine, Tryptophan, Tyrosine or preferably Proline;

$X_{27}$ is Alanine, Serine, Threonine, Isoleucine, Leucine, Glycine, or preferably Valine;

$X_{28}$ is Alanine, Serine, Threonine, Isoleucine, Leucine, Valine, or preferably Glycine;

$B_{29}$ is Asp, Glutamine, Histidine, Lysine, or preferably Arginine;

$X_{30}$ is Alanine, Glycine, Leucine Serine, Threonine, Isoleucine or preferably, Valine;

$B_{31}$ is Arginine, Lysine, Asparagine, Glutamine, or preferably Histidine;

$B_{32}$ is Arginine, Histidine, Asparagine, Glutamine, or preferably Lysine $X_{33}$ is Alanine, Glycine, Serine, Threonine, Isoleucine, Valine, or preferably Leucine;

$X_{34}$ is Alanine, Glycine, Serine, Threonine, Isoleucine, Valine, or preferably Leucine;

$B_{35}$ is Lysine, Histidine, Asparagine, Glutamine, or preferably Arginine;

B$_{36}$ is Arginine, Histidine, Asparagine, Glutamine, or preferably Lysine;

X$_{37}$* is Alanine, Glutamine, Serine, Threonine, Asparagine, or preferably Glycine Z$_{38}$ is Glutamine, Phenylalanine, Tryptophan, Tyrosine or preferably Asparagine; and Z$_{39}$ is Asparagine, Glutamine, Phenylalanine, Tryptophan, or preferably Tyrosine.

Typical compounds within the scope of the Buforinins are:

AlaGlyRArgGlyLysGlnGlyGlyLys-
ValArgAlaLysAlaLysThrArgSerSerArgAla GlyLeuGlnPheProV-
alGlyArgValHisArgLeuLeuArgLysGlyAsnTyr (SEQ ID NO:1)

ThrArgSerSerArgAlaGlyLeuGln-
PheProValGlyArgValHisArgLeuLeuArgLys (SEQ ID NO: 2)

ThrArgSerSerArgAlaGlyLeuGln-
PheProValGlyArgValHisArgLerLeuArgLysGlyAsnTyr (SEQ ID NO:3)

AlaGlyArgGlyLysGlnGlyGlyLys-
ValArgAlaLysAlaLysThrArgSerSerArgAlaGlyLeuGln PheProV-
alGlyArgValHisArgLeuLeuArglys (SEQ ID NO:4)

ThrArgAlaAlaArgAlaGlyLeuGln-
PheProValGlyArgValHisArgLeuLeuArgLys(SEQ ID NO:5),

ThrArgLeuLeuArgAlaGlyLeuGln-
PheProValGlyArgValHisArgValHisArgLeuLeuArgLys (SEQ ID NO:6)

"Active" Buforinins are defined as those peptides that fit the invention sequence description and inhibit BttxB and/or Tttx protease activities. The conformation of the Buforinins may be determined by circular dichroism and Fr-IR. See C̆anaves, J. M., et at. (1998) J. Biol. Chem. 273:43214–34221. Proton NMR may also be used. See Yi, G. et at. (1996) FEBS Lett. 398:87–90. X-ray crystallography may also be used. See Sutton, R. B., et al. (1998) Nature 395, 347–353.

"Derivatives" of Buforinins are defined as those peptides fitting the invention description that have amino acid modifications such as Buforinin peptides containing 'unnatural' amino acids other than the known 21 amino acids (20 common, and then selenocysteine, which is an uncommon but naturally occurring non-gene encoded amino acid) or additions such as cysteine and lysine on termini to provide a reactive center for conjugation to other chemicals, labels or proteins.

"Truncated" Buforinins include compounds of the formula (1) such as B-II. Amino acids can be truncated, asymmetrically, upstream and downstream while maintaining the helix-turn-helix supersecondary structure. B-II could be optimized by amino acid substitutions to promote a helical structure upstream of the QF site. See, e.g. SEQ ID NO:5 and SEQ NO:6.

Preparation of the Invention Compounds

The invention compounds, often designated herein "Buforinins" are essentially peptide backbones which may be modified at the N- or C-terminus.

Standard methods can be used to synthesize peptides similar in size and conformation to the Buforinins. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis.

In addition to providing the peptide backbone, the N- and/or C-terminus can be modified with conventional chemical techniques. The compounds of the invention may optionally contain an acyl or an acetyl group at the amino terminus. Methods for acetylating or, more generally, acylating, the fee amino group at the N-terminus are generally known in the art.

At the carboxy terminus, the carboxyl group may be present in the form of a salt; and in the case of pharmaceutical compositions, the salt will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of he relevant acid addition salts.

If the peptide backbone is comprised entirely of gene-encoded amino acids, or if some portion of it is so composed, the peptide or the relevant portion may also be synthesized using recombinant DNA techniques. The DNA encoding the peptides of the invention may be synthesized using standard techniques in the art such as solid phase DNA synthesis with conventional equipment that includes, for example, an ABI 3948 Nucleic Acid Synthesis System (Perkin Elmer Applied Biosystems, Foster City, Calif.) utilizing phosphoramidite synthesis chemistry (Beaucage, S. L. et al. (81) Tetrahedorn Lett. 22:19859–1862). DNA oligomers would be synthesized with overlapping matching complimentary sequences. Annealing of these sequences would form a double-stranded synthetic gene. Building on this process would give larger and larger double-stranded products till the requisite gene is built Alternatively, DNA recombinant means would be employed by cloning Buforinins, or like-fragment of H2A protein, and then modifying by site-directed mutagenesis or DNA cassette replacement or other means in the art (Methods Enzymology vol. 152; Eds. S. L. Berge and A. R. Kimmel, Academic Pres, Inc., Orlando, Fla., 1998) to achieve the modification desired. Codon choice can be integrated into the synthesis depending on the nature of the host.

For recombinant production, the DNA encoding the Buforinins is included in an expression system which places these coding sequences under the control of a suitable promoter and other control sequences which are compatible with an intended host cell. Types of host cells available span almost the entire range of the plant and animal kingdoms. Thus, the Buforinins of the invention could be produced in bacteria or yeast (to the extent that they can be produced in a nontoxic or refactile form or utilize resistant strains) as well as in animal cells, insect cells and plant cells.

The Buforninis can be produced in a form that will result in their secretion from the host cell by fusing to the DNA encoding the Buforinin, a DNA encoding a suitable signal peptide, or may be produced intracellularly. They may also be produced as fusion proteins with additional amino acid sequence which may or may not need to be subsequently removed prior to the use of these compounds as an inhibitor of BttxB protease activity.

Thus, the Buforinins of the invention can be produced in a variety of modalities including chemical synthesis and recombinant production or some combination of these techniques.

Any members of the Buforinin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

The invention is also directed to the screening assays for the Buforinin analogues and assays utilizing the analogues.

The invention is also directed to the use of Buforinins as intracellular inhibitors of BttxB. Bttxs specifically target nerve cells because of the receptor-like recognition of cell surface gangliosides and synaptogamin by the nerve-cell targeting heavy chain (HC) subunit of the toxin. See Kozaki, S., et al. (1998) Microb. Pathog. 25:91–99. Once bound, the toxin is internalized by a mechanism not completely understood but apparently requires acidification of the endosome and cleavage of the disulfide bond linking the HC and the endoproteolytically active light chain (LC).

The specificity of this delivery system would be useful for delivery of Buforinins to those cell types poisoned or potentially poisoned with BttxB and could be used as a 'magic bullet' since the magic bullet approach is becoming a reality. See e.g. Pastan, I., et al. (1994) Ann. Rev. Biochem. 61:331–354 and Enger, A., et al. (1998) Curr. Top. Microbial. Immnunol. 234:13–33 (Introduction of immunotoxins linked to Diptheria toxin or Ricin A chain).

Therefore, Buforonins may be linked to BttxB HC with a linkage such as a disulfide bond. Alternatively, Buforinins may be linked to BttxB HC with a carrier protein such as human albumin or another bridge to form a multi-protein conjugate. This conjugate should then target the susceptible cells in a manner similar to BttxB. Once inside the cell, the conjugate may inhibit BttxB or the linkage may be cleaved to free the Buforinins or carrier-Buforinins to inhibit BttxB.

Antibodies

Antibodies to the Buforinins may be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hasten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The Buforinins in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and $F(ab')_2$ fragments as well as modified immunoreactive forms such as Fv regions, which are produced by manipulation of the relevant genes (isolatable, for example, from the appropriate hybridoma).

The antibodies of the invention are, of course, useful in immunoassays for determining the amount or presence of the Buforinins. Such assays are essential in quality controlled production of compositions coining the Buforinins of the invention. In addition, the antibodies can be used to assess the efficacy of recombinant production of the Buforinins, as well as for screening expression libraries for the presence of Buforinin encoding gene. They may also be used as affinity ligands for purifying and/or isolating the Buforinins. They may also be used for detecting and measuring Buforinins in sera or plasma by methods well known in the art such as RIA and ELISA. Therefore, one may monitor circulating Buforinin levels to assure sufficient dosage.

Compositions Containing the Buforinins and Methods of Use

The Buforinins are effective in inhibiting the protease activity of BttxB and tetanus neurotoxins. Accordingly, they can be used in prevention, prophylaxis and therapies for BttxB and Tttx poisoning. For use in such contexts, a Buforinin may be administered alone, or a variety of Buforinins may be administered, or the Buforinin or the variety of Buforinins may be administered as a mixture with additional protease inhibitors or adjunct chemicals such as trisl2-carboxyethyl)phosphine (TCEP).

TCEP is a non-odorous, non-sulfhydryl containing reducing agent that is relatively non-toxic in animals $(P—CH_2CH_2COOH)_3HCl$; Molecular Probes, Inc. Eugene Oreg.). TCEP can reduce the disulfide bond between the HC and LC and allow the dissociation of the BttxB or Tttx subunits. TCEP would work on any BOT. This dissociation increases the availability of the active QF site to Buforinins. Additionally, the disassociation of the toxin prevents nerve cell penetration. Other reducing agents such as dithiothreitol (DTT) may be used; however, they may be objectionable due to their distinctive odors and toxicity. TCEP can be used in conjunction with chaotropes. Therefore, TCEP is preferred The peptides of the invention are also useful as standards in monitoring assays and in assays for evaluating the effectiveness of later-generation Buforinins. This could be done by utilizing the endopeptidase activity assay for BttxB. In this endopeptidase assay, one may evaluate whether potential peptides function as inhibitors or substrates of BttxB by the ability to cleave of a synthetic peptide substrate comprising amino acids 55–94 of the intracellular target VAMP2. The cleavage products may be separated by a $C_{18}$ reverse-phase HPLC column and detected by absorbance at 205 nm.

For preventing the initial intoxication or further poisoning caused by BttxB and Tttx in animal subjects, the Buforinins can be formulated as pharmaceutical or veterinary compositions Depending on the subject to be treated, the mode of administration, and the type of treatment desired—e.g., prevention, prophylaxis, therapy; the Buforinins arc formulated in ways consonant with these parameters. A summary of such techniques is found in *Remington's Pharmaceutical Sciences,* latest edition, Mack Publishing Co., Easton, Pa.

In general, for use in treatment or prophylaxis, the Buforinins may be used alone or in combination with other compounds which inhibit protease activity such as VAMP2. Use of the enantiomeric forms containing all D-amino acids may confer advantages such as resistance to those proteases, such as trypsin and chymotrypsin.

The Buforinins can be administrated singly or as mixtures of several Buforinins or in combination with other pharmaceutically active components, and in single or multiple administrations. The formulations may be prepared in a manner suitable for systemic administration. Systemic formulations include those designed for injection, e.g. intramuscular, intravenous or subcutaneous injection, or may be prepared for transdermal, transmucosl, or oral administration. The formulation will generally include a diluent as well as, in some cases, adjuvants, buffers, preservatives and the like. The Buforinins can be administered also in liposomal compositions or as microemulsions using conventional techniques.

If orally administered, the Buforinins of the invention must be protected from degradation in the stomach using a suitable enteric coating. This may be avoided to some extent by utilizing amino acids in the D-configuration, thus providing resistance to protease. However, the peptide is still susceptible to acid hydrolysis; thus, some degree of enteric coating may still be required.

The manner of administration and formulation of the compounds useful in the invention and their related compounds will depend on the nature of the condition, the severity of the condition, the particular subject to be treated, and the judgement of the practitioner, formulation will depend on mode of administration As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Suitable alternative formulations also include nasal sprays, liposomal formulations, slow-release formulations, and the like.

Any suitable formulation may be used. A compendium of art-known formulations is found in *Remington's Pharmaceutical Sciences,* latest edition, Mack Publishing Company, Easton, Pa. Reference to this manual is routine in the art.

A preferred means to deliver the Buforinins would include the use TCEP. Since TCEP cleaves the holotoxin which yields a site available to the Buforinin. TCEP also disassociates the toxins into individual components which prevents nerve cell penetration.

Also, the Buforinins could be coupled to a variety of compounds including a BttxB heavy chain, which excludes the toxin light chain, to target the Buforinin to the toxin affected cells.

The dosages of the compounds of the invention will depend on a number of factors which will vary from patient to patient The following examples are intended to illustrate but not to limit the invention

EXAMPLE 1

Endopeptidase Activity Assay

The toxin was activated immediately prior to use by incubating at 25° C. for 30 minutes in an activation mixture that contain in a volume of 7.5 $\mu$l per digest: 2.4 $\mu$g (16 pmol) of toxin, 30 mM NaHEPES buffer, pH 7.3, and 5 mM DTT or TCEP. A substrate peptide mix was prepared that contained 1 nmol of the substrate peptide (VAMP2 55–94), 4% DMSO, 4% Triton X-100, and 80 mM NaHEPES buffer, pH 7.3, per digest. The final reaction mix was made by adding 25 $\mu$l of the substrate peptide mix, 4.5 $\mu$l of fresh 10 mM DTT, 13 $\mu$l $H_2O$ or test peptide, and 7.5 $\mu$l of activation mixture. The reaction was initiated by incubation at 37° C. The reaction was stopped by the addition of 1 vol trifluoroacetic acid (TA) to 0.25%. The samples were clarified by centrifugation.

In this assay, 16 pmol of BttxB digested 1 nmol of the substrate to completion in less than 45 min. at37° C.

EXAMPLE 2

Reverse Phase HPLC Analysis of Digestion Products

Digested peptide products were fractionated by RP-HPLC on a Waters $\mu$Bondapak analytical $C_{18}$ column (3.9 mm×30 cm) attached to Beckman 126 pumps and a model 168 Diode Array Detector, controlled by Beckman System Gold Ver 8.1 software. The solvent system consisted of buffer A (BA; $H_2O$-0.1% TFA) and buffer B (BB; $CH_3CN$-0.1% TFA). The development program consisted of the following: 97% BA, 0–1 min; to 33% BB, 1–30 min; then wash with 97% BB for 5 min, followed by equilibration in 97% BA for 10 min. The flow rate was ml $min^{-1}$ except during the wash and equilibrium phase where it was 1.5 ml $min^{-1}$. 75 $\mu$l injections were made with a Waters Intelligent Sample Processor (WISP Model 712). The effluent was monitored at dual wavelengths of 205 and 280 nm.

Initially, digestion products are identified by peptide sequencing using automated Edman-degradation on an ABI 477A protein sequencer attached in-line with a HPLC (ABI model 120A) for detection of phenlythiohydration derivatized amino acids. The extent of digestion was determined by comparison of peak areas of undigested controls (no added toxin) and total digests (digests allowed to go to completion, typically 2–3 h). The extent of inhibition or digestion will be determined from e ion of the chromatograms by peak area comparison with standard and/or products formed compared with quantified standards or digests without added inhibitor that have gone to completion.

EXAMPLE 3

Secondary Structure Predictions

Secondary structures were predicted by using the nnpredict, and the Gibrat (GOR2) programs. See McCleland, D. G, Rumelhart D. E. In Explorations in Parallel Distributed Processing. vol. 3:318–362.1988. MIT Press, Cambridge Mass.; Kneller D. G., et at. (1990) J. Mol. Biol. 214:171–182; Gamier, J. et al. (1978) J. Mol. Biol 198,425–443; Garnier J. et al. (1987) J. Mol. Biol. 120:97–120; Gamier, J., et al. (1996) Methods Enzymol. 266:540–553. Helical wheel projections were made using the Anthprot program Ver 4. See Deleage, G., Instit de Biologie et Chimi des Protéins, Lyon, France.

The Gibrat program predicts that B-I could form an α-helical-turn-α-helical configuration similar to that of VAMP2. See Table 3. The result that Buforin I may form a secondary structure similar to VAMP2 then suggests that B-I may also form a similar supersecondary structure of a reverse turn with helix bundling similar to VAMP2. See Lebeda, et. al. (1996). In support of this prediction, it was found that the diminishing inhibition of BttxB activity and its helical content as Buforin-I was truncated, mirrors the diminishing activity of BttxB for substrate deletions. See data for Buforin-II in Table 1 and FIG. 4.

EXAMPLE 4

Preparation of Bufornins

The Buforinins may be obtained from amphibian stomach by gut lavage using methods as described by Park, C. B. et al. See Park, C. B., et al. (1996) Biochem. Biophys. Res. Comm. 218:408–413.

The Bufornins may be synthesized by solid-phase peptide synthesis (SSPS) as described by L. A. Carpino, J. Am. Chem. Soc. 79,4427 (1957), C. D. Chang et al., Int. J. Pept. Protein Res. 11, 246 (1978), E. Atherton, et al., J. Chem Soc. Chem. Commun, 537 (1978) and R. B. Merrifield, J. Am Chem. Soc. 85,2149 (1963) and Barlos, K, et al., (1989) Tetrahedron Lett. 30:3947.

The Buforinins may also be produced by DNA recombinant means commonly known in the art whereby a suitable promoter for expression in heterologous systems, i.e. bacterial, fungi, insect, or mammalian cell cultures may be used. The DNA sequence may be optimized for the particular host and tRNA content.

EXAMPLE 5

Inhibition of Protease Activity by Buforinins

The endopeptidase assay and reverse phase HPLC as described in Examples 1 and 2 may be used to detect the cleavage products and the extent of protease inhibition Briefly, potential inhibitors may be added to the substrate peptide mix immediately before the addition of the activation mix containing the toxin as described in Garica, et al. After incubation for 45 min at 37° C., the reaction should be stopped and the digestion products may be analyzed by using RP HPLC. If a fluorescent-labeled substrate is used then product formation will be determined with an in-line fluorescent detector.

The extent of inhibition or digestion will be determine as described in Example 2 of undigested substrate remaining and/or products formed compared with quantified standards or digests without added inhibitor that have gone to completion.

Alternative means can be used include densitometry wherein the substrates and products separated by electrophoresis and stained with protein specific dyes, i.e. Coomassie brilliant blue, and measured. One may also perform immunoassays to determine the extent of inhibition or digestion by utilizing substrate or product specific antibodies.

Alternatives also include in vivo protection or tissue specific function assays. For example, an experimental animal would be dosed with the inhibitor with or with out adjuncts and then challenged with the toxin, e.g. i.v. injection of a Buforinin with a reducing agent such as TCEP. The onset of symptoms or an alteration of the $LD_{50}$ would then be evaluated. Tissue protection assays would employ an intact nerve-muscle preparation wherein muscle twitch response to nerve cell stimulation would be evaluated The toxin would be preincubated with a Buforinin and adjuncts and are then added to the tissue preparation.

EXAMPLE 6

Designing Buforinins with an Effect on BttxB Protease Activity

By using standard methods and techniques the peptides of the invention may be modified by either making mutations or substitutions which include substituting $Pro_{26}$ with glutamine to make the active site more like the substrate, or other amino acid, that favors turn formation without the turn constraint imposed by Pro. Such substitutions are predicted to result in more effective helix bundling for toxin association to occur. Other amino acid substitutions or mutations in the helix region could be made so that either the helix becomes more amphipathic to improve helix bundling or improve interaction with the toxin. Such changes would include a substitution of R11 with L or another helix favoring amino acid. See FIGS. 6A and B. Similarly, multiple substitutions R11L, K15L, and S18L or other amino acids could be made to favor helix formation and bundling.

Alternatively, B-II which lacks the predicted upstream helix of B-I may be modified to enhance and improve its ability to inhibit BttxB protease activity. For example, a peptide having substitutions S3A and S4A (SEQ ID NO:5) has a predicted helix upstream of the QF site. Another example would be a peptide having substitutions S2L and S4L (SEQ ID NO:6). Likewise, this peptide has a predicted helix upstream of the QF site.

EXAMPLE 7

Buforinin Pretreatment

Buforinins may be used to pretreat food and liquids that might be contaminated with BttxB or Tttx. For example, an effective amount of a Buforinin may be mixed into water having BttxB to inhibit the protease activity of the BttxB, e.g. 100 ml of water containing 1 ug of BttxB would be treated with 100 ug of Buforinin and 0.1 mmol reducing agent, i.e. TCEP in tablet, powder, or liquid form.

These various forms would comprise of a Buforinin reducing agent such as TCEP, and other fillers and stabilizers. A liquid form could be made from a tablet or powder that is pre-dissolved prior to use. A Buforinin solution may be applied on the surface of solid food having BttxB on the surface. Alternatively, an effective amount of a Buforinin may be used to treat solid food which has been ground into small particles in order to allow the Buforinin access to amounts of BttxB which is not found on the surface of the food.

Contaminated or suspect non-food surfaces may also be washed with solutions of Buforinin Buforinins could be applied as a spray, foam, towelette, or sponge used to soak or wipe the surface. The amounts would be typically 200 ug per ml of solution applied; however, the concentrations required would depend on the extent of contamination and the appropriate Buforinin concentration may be adjusted as needed.

EXAMPLE 8

Prophylaxis Uses

Buforinins could be used as a prophylactic against BttxB or Tttx poisoning. Subjects could be treated with Buforinins prior to entering situations where they are likely to be in contact with BttxB or Tttx. The dosage mode and amount could be dependent on the amount of toxin expected to contact and the time in which contact might occur. The preferred administration for immediate contact would be i.v. The preferred form administration for a slower and more prolonged exposure would be by ingestion However, other slow release forms of delivery such as a patch may be used.

EXAMPLE 9

Prevention of Aerosol Contamination

Buforinins may be incorporated into a disposable, moist-filter, breathing mask for inactivating BttxB in aerosol form. The toxin would be trapped in moist-filter whereupon it would inactivated by a Buforinin.

Such a filter design would protect against toxin particles smaller than bacteria, e.g. 1 micron such as HEPA. The filters could be supplied premoistened and impregnated with Buforinins and adjunct chemicals such as TCEP. Alternatively, the filters could be prepared by wetting a dry filter pre-impregnated or by soaking the filter in a solution of Buforinins. Enclosed areas that have air processing capabilities may also be protected in this fashion with appropriate sized filters.

EXAMPLE 10

Wound Treatment

Open lesions could be treated with topical applications having Buforinins to inhibit BttxB or Tttx poisoning before the toxin has a chance to be absorbed into the body. A powder mixture containing Buforinins and adjuncts which include a reducing agent and other stabilizers or fillers may be applied directly to the wound. This approach relies on the wound weeping to dissolve the Buforinin Alternatively, an ointment, liquid, spray, foam, or towelette having Buforinins may be applied to the wound su. The towelette could be supplied or made in a similar manner as the filters of Example 10.

EXAMPLE 11

Post Exposure

Subjects already suffering from BttxB or Tttx poisoning could be treated with Buforinins. These of treatments would scavenge accessible toxin not yet compartmentalized into susceptible cells. Intoxication of susceptible cells leads to cell function inhibition but is not itself lethal to the cells. Given sufficient time the cells can recover and become functional again. This recovery process may last up to several months. Therefore, treatment with Buforinins will aid in the recovery of the subject and reduce the need of alternative life supporting measures. The treatment may comprise use of Buforinin-BttxB HC or other like conjugates. The Bttx-HC portion would specifically direct the conjugate to susceptible cells where uptake would occur in a manner similar as the toxin. Inside the cell, the Buforinins would access to the toxin and inhibit the protease activity, thereby protecting the cell against further toxin damage until the toxin is removed from the cells by endogenous proteolysis.

EXAMPLE 12

Identification of a Botulinum Toxin Subclass

Buforinins may be used for the identification of BttxB or Tttx An unknown Bttx or Tttx would be incubated with substrates and a Buforinin that would specifically inhibit BttxB and Tttx if present. Detection of uncleaved substrate or reduction of digest products would allow the identification of the toxin.

This may be useful as a confirming assay since the inhibition is specific. For example, a C-terminal fluorescent-labeled substrate, such as VAMP2, would be attached to microtiter plates See Hallis, B., et al. (1996) J. Clin. Microbiol. 34:1934–1938. The unknown sample is then added to the well and allowed to incubate. The reaction would be stopped and the well rinsed. Reduction of fluorescence would indicate susceptibility of the substrate to the toxin If Buforinins are included in the digest mix then BttxB or Tttx toxin would be specifically inhibited and the fluorescence levels would be higher than those rations containing BttxB without inhibitor.

EXAMPLE 13

Long-lived Peptide in vivo

Figure 7:
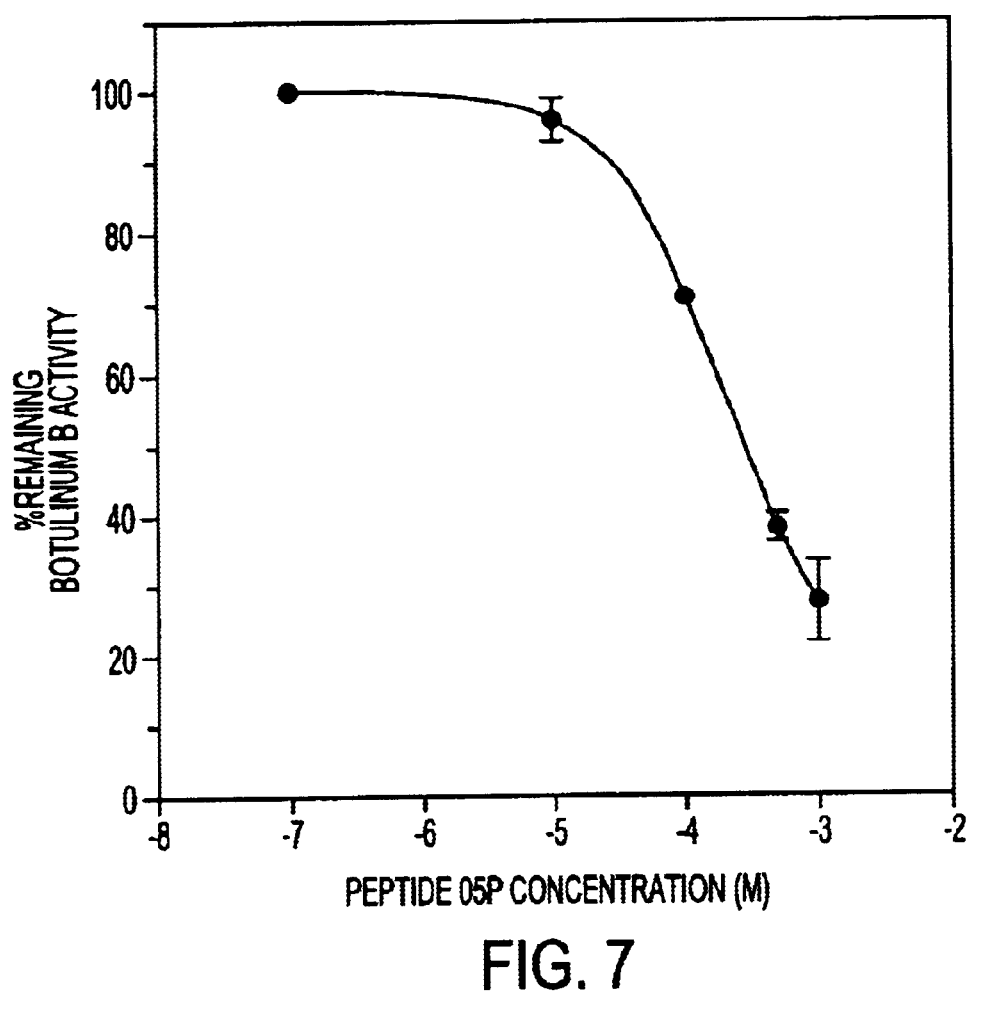

To establish efficacy for the use of buforin I as treatment of botulinum B toxicity, the pharmacokinetic parameters of buforin I in the blood were examined. Since human studies are not possible, a rat model was used Buforin I was injected intraperitoneally at a dose of 100 ng/kg containing radiolabeled $^{125}$I-buforin 1 (2,000 Ci/mmol) as a tracer with the radioactive dose constant at 11 $\mu$Ci/kg. Blood (100 $\mu$l) was collected at timed intervals from the tail vein and flash frozen on dry-ice. At the time of analysis, the blood was quickly thawed and spiked with 1 $\mu$g of cold buforin 1, and the cells were lysed and solubilized by the addition of NCS tissue solubilizer. CPM (counts per minute) were determined for 20 $\mu$l aliquots in a Packard Tri-Carb and the results are shown in FIG. 7. The pharmacokinetic parameters are shown in Table 4.

The results show that there is a rapid uptake of buforin I into the blood stream over time. See FIG. 8. The time to reach ½ the absorbed maximal value is 7.7 minutes. The maximal-plateau level was reached within 40 min and was maintained for up to 4 h. The relatively minor differences in absolute responses between the two animals are probably due to injection variation or animal variability, nevertheless, both animals display a long steady stale level of buforin 1.

These results indicate that buforin I would have a long life in vivo and therefore be an effective therapeutic agent since it is distributed to the blood in a rapid manner and the level of buforin I persists over time at a high steady-state level.

TABLE 4

| Pharmacokinetic characteristics of $^{125}$I-buforin I after IP Injection | | |
|---|---|---|
| | Mean ± SEM | n |
| Bmax | 182.6 ± 50.0 CPM | 2 |
| Bmax | 7.7 ± 0.2 min | 2 |
| Plateau | 40 min | 2 |

EXAMPLE 14

Phosphorylation of Peptides

Phosphorylation provides peptides with additional properties that could improve the circulatory half-life, solubility, resistance to degradation, and the interaction of the peptide with the active site of the toxin, making it a more potent inhibitor. Indeed, the natural substrate VAMP2 has been found to be a good phosphorylation substrate and whose function may be affected by its phosphorylation state (Neilander, H B, et al. (95) J. Neurochem. 65:1712–20). Another possible mechanism for inhibition of toxin protease activity by phosphorylated amino acids i.e., phospho-Ser, -Thr and/or -Tyr, would be that once the peptide enters the active site of the toxin, the strong charge associated with the phosphate group might form a salt linkage with the zinc found in the active site of the toxin. This binding then would block access of the natural proteins to the catalytic site of the toxin, neutralizing the toxic effects of the molecule. Peptides containing phospho-Ser, -Thr and/or -Tyr(s) can be readily made during solid phase peptide synthesis (White, P and Beythien, J. in "Innovations & Perspectives in Solid Phase Synthesis & Combinatorial Libraries, 4h International Symposium", Epton, R. (Ed.), Mayflower Scientific Ltd., Birmingham 1996, pp. 557; Wakamiya, T., et al. Chem Lett, 1099 (1994)), or after synthesis by incubating the peptide with kinases specific for each of these amino acids (Risinger, C., Bennett, M K. (99) . Neurochem. 72:614–24).

EXAMPLE 15

General Botulinum Toxin/Tetanus Toxin Inhibitor in vivo

Use of TCEP and Chaotropes

Disruption of non-covalent interactions between the light and heavy chains of neurotoxins. A replacement for the foul-smelling and toxic sulfhydryl reducing agents such as 2-mercaptoethanol that functions equivalently to activate the neurotoxin in vitro was found. Once treated with TCEP, the disulfide bond covalently joining the heavy and light chains is broken. However, the neurotoxin chains apparently remain together due to strong hydrophobic interactions. In conjunction with TCEP, the use of biocompatible chaotropes will aid in completely separating holotoxins into its two chains, then the light chain would be effectively diluted in the body and could not target neuronal cells (or other cell types). Some biocompatible chaotropes include hydroxyurea or 2-oxo-1 pyrrolidine acetamide, compounds that are used for treatment of sickle cell anemia The combination of TCEP and biocompatible chaotropes to open the active site of all botulinum serotypes and similar toxins to pharmacological intervention before translocation into target cells will provide more effective and serotype nonspecific therapeutic peptides.

Incorporation by Reference

To the extent necessary to understand or complete the disclosure of the preset invention, all publications, patents, and patent applications mentioned herein are expressly incorporated by reference therein to the same extent as though each were individually so incorporated.

What is claimed is:

1. A pharmaceutical composition for treating botulinum or tetanus toxin poisoning which comprises a biocompatible chaotrope and an endoprotease inhibiting amount of a compound selected from the group consisting of AlaGlyArgGlyLysGlnGlyGlyLys-
        ValArgAlaLysAlaLysThrArgSerSerArgAlaGlyLeuGlnPhePro
        ValGlyArgValHisArgLeuLeuArgLysGlyAsnTyr (SEQ ID NO:1)

ThrArgSerSerArgAlaGlyLeuGln-
        PheProValGlyArgValHisArgLeuLeuArgLys (SEQ ID NO:2),

ThrArgSerSerArgAlaGlyLeuGln-
        PheProValGlyArgValHisArgLeuLeuArgLysGlyAsnTyr (SEQ ID NO:3),

AlaGlyArgGlyLysGlnGlyGlyLys-
        ValArgAlaLysAlaLysThrArgSerSerArgAlaGlyLeuGlnPhePro
        ValGlyArgValHisArgLeuLeuArgLys (SEQ ID NO:4) and the amidated forms thereof.

2. The pharmaceutical composition of claim 1, wherein the purified and isolated form is a phosphate salt.

3. The pharmaceutical composition of claim 2, wherein the phosphate salt is formed by the phosphorylation of Ser, Thr or Tyr.

4. The pharmaceutical composition of claim 1, further comprising tris-(2-carboxyethyl) phosphine (TCEP).

5. The pharmaceutical composition of claim 1, wherein the biocompatible chaotrope is hydroxyurea or 2-oxo-1 pyrolidine acetamide.

6. A method for treating botulinum or tetanus toxin poisoning comprising administering to a subject suspected of having botulinum or tetanus toxin poisoning an amount of a compound for a time and under conditions effective to inhibit the toxin poisoning, wherein the compound is selected from the group consisting of AlaGlyArgGlyLysGlnGlyGlyLys-
        ValArgAlaLysAlaLysThrArgSerSerArgAlaGlyLeuGlnPhePro
        ValGlyArgValHisArgLeuLeuArgLysGlyAsnTyr (SEQ ID NO:1), ThrArgSerSerArgAlaGlyLeuGln-
        PheProValGlyArgValHisArgLeuLeuArgLys (SEQ ID NO:2), ThrArgSerSerArgAlaGlyLeuGln- PheProValGlyArgValHisArgLeuLeuArgLysGlyAsnTyr (SEQ ID NO:3), AlaGlyArgGlyLysGlnGlyGlyLys-ValArgAlaLysAlaLysThrArgSerSerArgGlyLeuGlnPhePro ValGlyArgValHisArgLeuLeuArgLys (SEQ ID NO:4), ThrArgAlaArgAlaGlyLeuGlnPhePro ValGlyArgValHisArgLeuLeuArgLys (SEQ ID NO:5), ThrArgLeuLeuArgAlaGlyLeuGln-PheProValGlyArgValHisArgLeuLeuArgLys (SEQ ID NO:6), and the amidated forms thereof.

7. The method of claim 6, wherein the compound is administered to the subject prior to the subjects contact with Botulinum or tetanus intoxication.

8. The method of claim 7, wherein the Botulinum or tetanus intoxication results from aerosol contamination.

9. The method of claim 8, wherein the administration involves impregnating a filter with the compound and affixing it to the subject.

10. The method of claim 9, wherein the filter is a breathing filter.

11. The method of claim 6, wherein the compound is administered directly to a wound on the subject.

12. The method of claim 6, wherein the compound is conjugated to botulinum toxin heavy chain (Bttx-HC).

\* \* \* \* \*

SEQUENCE LISTING

```
<160> NUMBER OF SEQ ID NOS: 14

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 1

Ala Gly Arg Gly Lys Gln Gly Gly Lys Val Arg Ala Lys Ala Lys Thr
  1               5                  10                  15

Arg Ser Ser Arg Ala Gly Leu Gln Phe Pro Val Gly Arg Val His Arg
             20                  25                  30

Leu Leu Arg Lys Gly Asn Tyr
         35

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 2

Thr Arg Ser Ser Arg Ala Gly Leu Gln Phe Pro Val Gly Arg Val His
  1               5                  10                  15

Arg Leu Leu Arg Lys
             20

<210> SEQ ID NO 3
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 3

Thr Arg Ser Ser Arg Ala Gly Leu Gln Phe Pro Val Gly Arg Val His
 1               5                  10                  15

Arg Leu Leu Arg Lys Gly Asn Tyr
            20

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 4

Ala Gly Arg Gly Lys Gln Gly Gly Lys Val Arg Ala Lys Ala Lys Thr
 1               5                  10                  15

Arg Ser Ser Arg Ala Gly Leu Gln Phe Pro Val Gly Arg Val His Arg
            20                  25                  30

Leu Leu Arg Lys
            35

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 5

Thr Arg Ala Ala Arg Ala Gly Leu Gln Phe Pro Val Gly Arg Val His
 1               5                  10                  15

Arg Leu Leu Arg Lys
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      buforinin

<400> SEQUENCE: 6

Thr Arg Leu Leu Arg Ala Gly Leu Gln Phe Pro Val Gly Arg Val His
 1               5                  10                  15

Arg Leu Leu Arg Lys
            20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide 05P

<400> SEQUENCE: 7
```

```
Thr Arg Ser Arg Ala Lys Gly Leu Gln Phe Pro Gly Leu Leu Val His
 1               5                  10                  15

Arg Leu Leu Arg Lys Gly Asn Tyr
                20
```

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      VAMP2

<400> SEQUENCE: 8

```
Glu Arg Asp Gln Lys Leu Ser Glu Leu Asp Asp Arg Ala Asp Ala Leu
 1               5                  10                  15

Gln Ala Gly Ala Ser Gln Phe Glu Thr Ser Ala Ala Lys Leu Lys Arg
                20                  25                  30

Lys Tyr Trp Trp Lys Asn Leu Lys
                35                  40
```

<210> SEQ ID NO 9
<211> LENGTH: 38
<212> TYPE: PRT
<213> ORGANISM: Bufo bufo gagarizans

<400> SEQUENCE: 9

```
Gly Arg Gly Lys Gln Gly Gly Lys Val Arg Ala Lys Ala Lys Thr Arg
 1               5                  10                  15

Ser Ser Arg Ala Gly Leu Gln Phe Pro Val Gly Arg Val His Arg Leu
                20                  25                  30

Leu Arg Lys Gly Asn Tyr
                35
```

<210> SEQ ID NO 10
<211> LENGTH: 38
<212> TYPE: PRT
<213> ORGANISM: Gallus gallus

<400> SEQUENCE: 10

```
Gly Arg Gly Lys Gln Gly Gly Lys Ala Arg Ala Lys Ala Lys Ser Arg
 1               5                  10                  15

Ser Ser Arg Ala Gly Leu Gln Phe Pro Val Gly Arg Val His Arg Leu
                20                  25                  30

Leu Arg Lys Gly Asn Tyr
                35
```

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      buforin (truncated)

<400> SEQUENCE: 11

```
Gln Gly Gly Lys Val Arg Ala Lys Ala Lys Thr Arg Ser Ser Arg Ala
 1               5                  10                  15

Gly Leu Gln Phe Pro Val Gly Arg Val His Arg Leu Leu
                20                  25
```

<210> SEQ ID NO 12

-continued

```
<211> LENGTH: 39
<212> TYPE: PRT
<213> ORGANISM: Artificial Sequence
<220> FEATURE:
<223> OTHER INFORMATION: Description of Artificial Sequence: Synthetic
      B-I R11L

<400> SEQUENCE: 12

Ala Gly Arg Gly Lys Gln Gly Gly Lys Val Leu Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      B-I R11L, K15L, S18L

<400> SEQUENCE: 13

Ala Gly Arg Gly Lys Gln Gly Gly Lys Val Leu Ala Lys Ala Leu Thr
1               5                   10                  15

Arg Leu Ser Arg Ala Gly Leu Gln Phe Pro Val Gly Arg Val His Arg
            20                  25                  30

Leu Leu Arg Lys Gly Asn Tyr
        35

<210> SEQ ID NO 14
<211> LENGTH: 25
<212> TYPE: PRT
<213> ORGANISM: Gallus sp.

<400> SEQUENCE: 14

Lys Ser Arg Ser Ser Arg Ala Gly Leu Gln Phe Pro Val Gly Arg Val
1               5                   10                  15

His Arg Leu Leu Arg Lys Gly Asn Tyr
            20                  25
```